United States Patent [19]
Maier et al.

[11] Patent Number: 6,162,449
[45] Date of Patent: *Dec. 19, 2000

[54] SCLEROGLUCANS AND COSMETIC COMPOSITION CONTAINING THE NEW COMPOUNDS

[75] Inventors: Thomas Maier, Schliengen; Klaus Huber, Bad Lippspringe; Udo Rau, Dettum, all of Germany; Bernhard Schilling, Waltham, Mass.

[73] Assignee: Ciba Specialty Chemicals Corporation, Tarrytown, N.Y.

[ * ] Notice: This patent is subject to a terminal disclaimer.

[21] Appl. No.: 09/109,414

[22] Filed: Jul. 2, 1998

[30] Foreign Application Priority Data

Jul. 4, 1997 [GB] United Kingdom ............... 9714102

[51] Int. Cl.⁷ ........................................ A61K 7/00
[52] U.S. Cl. .................. 424/401; 424/78.03; 514/23; 514/54; 536/123.1; 536/123.12
[58] Field of Search ................ 424/401, 78.03; 514/23, 54, 937, 938; 536/123.1, 123.12

[56] References Cited

U.S. PATENT DOCUMENTS

| | | | |
|---|---|---|---|
| 3,301,848 | 1/1967 | Halleck | 260/209 |
| 5,536,493 | 7/1996 | Dubief | 424/70.13 |
| 5,574,023 | 11/1996 | Shibata et al. | 514/54 |
| 5,814,341 | 9/1998 | Frankhauser et al. | 424/493 |

FOREIGN PATENT DOCUMENTS

| | | |
|---|---|---|
| 0453366 | 10/1991 | European Pat. Off. . |
| 2050825 | 1/1981 | United Kingdom . |
| 94/04163 | 3/1994 | WIPO . |

OTHER PUBLICATIONS

Derwent Abstr. 91–256625.

*Primary Examiner*—Thurman K. Page
*Assistant Examiner*—Lakshmi Channavajjala
*Attorney, Agent, or Firm*—Kevin T. Mansfield

[57] ABSTRACT

A cosmetic composition is provided comprising:
A) a cosmetically acceptable carrier; and
B) 0.05 to 3.0 % by weight, based on the weight of the total composition, of a β-1,3-scleroglucan having a three-dimensional crosslinked triple helix structure and having a mean molecular weight of $1 \times 10^6$ to $12 \times 10^6$.

8 Claims, No Drawings

SCLEROGLUCANS AND COSMETIC COMPOSITION CONTAINING THE NEW COMPOUNDS

The present invention relates to new compounds, to processes for the production of the new compounds and to cosmetic compositions containing the new compounds as an active ingredient.

In GB-A-2 050 825 there is described a skin cosmetic composition of the oil-in-water type, comprising an emulsifying agent, an oil and water, the emulsifying agent being composed of a) at least one specified glycyrrhizic compound and b) at least one water-soluble polysaccharide selected from pectin, karaya gum, locust bean gum and xanthan gum.

The polysaccharides used in GB-A-2,050,825 have certain disadvantages, namely that they contain acidic groups, rendering them sensitive to salt formation and/or variations in pH, as well as a lack of stability over an adequate temperature range.

In JP030167109 there is described a cosmetic material containing a β-1,3-glucan having a mean molecular weight greater than $10\times10^6$. β-1,3-glucans having a mean molecular weight greater than $10\times10^6$, however, are of poor aspect, and their molecular weight cannot be determined using the conventional light scattering method.

It has now been found that certain new scleroglucans are useful as active ingredients and as excipients in cosmetic compositions, without the disadvantages associated with the polysaccharides used in GB-A-2,050,825 or with the β-1,3-glucans of JP030167109. Moreover, the scleroglucans used in the present compositions, on drying, form flexible films which, although insoluble in water, swell readily therein. This ability to form films represents an added advantage for the use of these scleroglucans in cosmetic formulations. Still further, the new scleroglucans have been found to exhibit valuable anti-inflammatory properties, rendering them valuable, for example, as active ingredients in after-sun preparations for the treatment of sun burn.

Accordingly, the present invention provides, as a first aspect, a cosmetic composition comprising:

A) a cosmetically acceptable carrier; and
B) 0.05 to 3.0, preferably 0.2 to 1.0% by weight, based on the weight of the total composition, of a β-1,3-scleroglucan having a three-dimensional crosslinked triple helix structure and having a mean molecular weight of $1\times10^6$ to $12\times10^6$, preferably $2\times10^6$ to $10\times10^6$.

The cosmetic composition may constitute, e.g., a shampoo and/or hair conditioner composition, in which the scleroglucan component B) may perform one or more of the following functions:

i) effect an improvement in the combability of hair treated with the shampoo/conditioner;
ii) effect an improvement in the dispersion of other components in the shampoo/conditioner;
iii) act as a smoothing agent for hair treated with the shampoo/conditioner; and
iv) effect an improvement in the level of fixing of such additives as dyes or UV absorbers in the shampoo/conditioner.

The cosmetic composition according to the present invention may also constitute a skin care composition, e.g., an emulsion or cream in which the scleroglucan may perform one or more of the following functions:

i) effect a lubricating function, thereby facilitating the spreading of the composition on the skin;
ii) act as a film-forming agent, thereby providing a protective film on the skin, which film, while almost undetectable by touching, provides the skin with a silky feel;
iii) effect a smoothing of the skin by reducing the scaling of the outermost layer of stratum corneum;
iv) effect an anti-inflammatory effect on the skin;
v) effect an improvement in the dispersion of other components of the skin care composition; and
vi) act as an emulsifier or co-emulsifier for the skin care composition.

The skin care composition may be formulated as an aqueous lotion, a water-in-oil or an oil-in-water emulsion, an oil or oil-alcohol lotion, a vesicular dispersion of anionic or nonionic amphiphilic lipids, an aqueous, aqueous-alcohol, alcohol or oil-alcohol gel, a solid stick or an aerosol formulation.

When formulated as a water-in-oil or an oil-in-water emulsion, the cosmetically acceptable carrier A) preferably comprises 5 to 50% of an oil phase; and 47 to 94.95% of water, each based on the total weight of the composition.

The oil phase may comprise any oil, or mixture thereof, which is known to be suitable for use in cosmetic compositions.

Examples of such oils include aliphatic hydrocarbons such as liquid paraffin, squalane, vaseline and ceresin; vegetable oils such as olive oil, almond oil, sesame oil, avocado oil, castor oil, cacao butter and palm oil; animal oils such shark liver oil, cod liver oil, whale oil, beef tallow and butter fat; waxes including bees wax, carnauba wax, spermaceti and lanolin; fatty acids such as lauric acid, myristic acid, palmitic acid, stearic acid, oleic acid and behenic acid; aliphatic alcohols such as lauryl alcohol, stearyl alcohol, cetyl alcohol and oleyl alcohol; and aliphatic esters such as isopropyl-, isocetyl- or octadecyl myristate, butyl stearate, hexyl laurate, diisopropyl adipate or diisopropyl sebacate.

Preferred mono- or polyols, for use in an oil-alcohol lotion, or a an oil-alcohol or alcohol gel, include ethanol, isopropanol, propylene glycol, hexylene glycol, glycerine and sorbitol.

When the β-1,3-scleroglucan is used as a co-emulsifier, the other emulsifier used may be any emulsifier conventionally used in cosmetic formulations e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic composition according to the present invention may constitute an anti-inflammatory skin care preparation, especially an after-sun skin care preparation.

The cosmetic composition according to the present invention may also constitute an oral care preparation, e.g., a dental gel, a denture fixation aid or a tooth paste; a mucosal lubricant formulation such as a vaginal cream or gel; or an ophthalmological preparation such as eye drops; in which the glucan component B) may perform one or more of the following functions:

i) effect lubrication of dry mucosae;
ii) effect thickening of liquid preparations;
iii) effect retention of active ingredients by formation of films on mucosal surfaces; and
iv) effect an improvement in the dispersion of other components in the composition.

When the β-1,3-scleroglucan is used in an ophthalmological preparation, it may be used together with other components such as:

a) ophthalmological active ingredients e.g. Gentamicin sulphate, Lomefloxacin hydrochloride, Chloramphenicol, Sodium Diclofenac, Potassium Diclofenac, Dexamethason di-sodium phosphate, Naphazolin nitrate, Tetryzolin hydrochloride, Antazolin hydrochloride, Antazolin sulphate, Pilocarpin chloride, Vitamin A-palmitate and zinc sulphate;

b) ophthalmological buffers such as boric acid, borax, acetic acid, sodium acetate, phosphoric acid, sodium dihydrogen phosphate, disodium hydrogen phosphate, sodium phosphate, Trometamol, citric acid and sodium citrate;

c) ophthalmological preservatives such as benzyl alkylammonium chloride, benzoxonium chloride, chlorhexidine digluconate, chlorobutanol, phenylethyl alcohol and Thiomersal;

d) solvents such as ethanol, glycerol, polyethylene glycol and water or mixtures thereof;

e) solution aids such as Cremophor EL, Cremophor RH, Tween 20 and Tween 80;

f) isotonising agents such as sodium chloride, mannitol and sorbitol, g) chelate formers such as disodium EDTA;

h) antioxidants such as α-tocopherol acetate, ascorbic acid, N-acetyl-cystine, sodium bisulphite, sodium thiosulphate and propyl gallate; and i) viscosity-increasing compounds such as methylhydroxypropyl cellulose, saccharose, Carbopol 934P, Carbopol 940, Carbopol 980 and Polaxomer F 127.

The cosmetic composition according to the present invention may also be used as lubricant.

The cosmetic composition of the invention may also comprise further components which are known to perform a useful function in a cosmetic composition. Examples of such further components include, e.g., emollients, skin moisturizers, UV absorbers such as an oxanilide, a triazine or triazole, additional thickening agents such as xanthan, moisture-retention agents such as glycerine, film formers, preservatives, perfumes and colourants.

The β-1,3-scleroglucan component of the cosmetic composition of the present invention has three-dimensional structure of crosslinked triple helices and contains in its structure β-1,3-bonded glucopyranose as the main chain and β-1,6-bonded glucopyranose as side chains and has the structural formula:

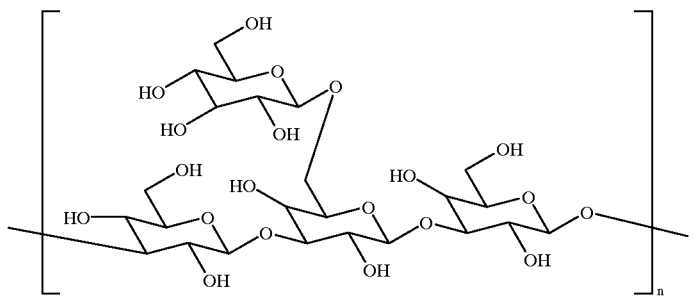

in which n is a number which provides the β-1,3-scleroglucan component with a mean molecular weight (MW) of $1\times10^6$ to $12\times10^6$, preferably $2\times10^6$ to $10\times10^6$, determined from the readily measured Staudinger Index η using the following Mark-Houwink equation:

$$MW=[\eta/4\times45\times10^{-7}]^{1/1.49}.$$

Preferably, a 0.3 g/l aqueous solution of the β-1,3-scleroglucan has a glucose content below 0.1 g/l and a viscosity of 50 to 190 mPa.s, measured at a shear rate of 0.3 $s^{-1}$ at 20° C.

The β-1,3-scleroglucan having a mean molecular weight of $1\times10^6$ to $12\times10^6$, preferably $2\times10^6$ to $10\times10^6$, and having a three-dimensional crosslinked triple helix structure is a new composition of matter and, as such, constitutes a second aspect of the present invention.

The molecular characterisation of the β-1,3-scleroglucan may be conveniently conducted by light scattering techniques using different polymer concentrations in a suitable solvent such as 0.01N aqueous sodium hydroxide. For example, a stock solution may be produced from a freeze-dried, powdered β-1,3-scleroglucan sample and the stock solution may then be stirred for 1–2 days at 25° C. The static and dynamic light scattering parameters may then be determined. From these values, there may be derived the ratio $(R_g/R_h)$ of the radius of gyration $(R_g)$ to the hydrodynamic radius $(R_h)$. This ratio $(R_g/R_h)$ serves as an indication of the shape of the test sample.

Viscosity measurements may then be carried out at 25° C. on various diluted samples of the stock solution using aqueous sodium hydroxide or dimethylsulfoxide as solvent. A suitable instrument for conducting the viscosity measurements is the Ubbelohde-Capillary I (capillary constant K=0.009693), with the application of the Hagenbach correction.

These molecular characterisation techniques demonstrate that the new β-1,3-scleroglucan is present as physically connected triple helices at 25° C.

The β-1,3-scleroglucan is produced using the plant-pathogenic fungi imperfecti Sclerotium rolfsii ATCC 15205. This process forms a third aspect of the present invention.

The process of the invention is characterized in that microorganisms, in the form of the plant-pathogenic fungi imperfecti Sclerotium rolfsii ATCC 15205 are cultivated in a culture medium under microaerobic conditions.

The basic cultivation medium used may be that described in U.S. Pat. No. 3,301,848 comprising a carbon source; a nitrogen source such as an ammonium salt or, preferably, sodium nitrate; a phosphate source such as dipotassiumhydrogen phosphate trihydrate; potassium chloride; magnesium sulfate heptahydrate; ferric sulfate heptahydrate; and yeast extract. The use of dipotassiumhydrogen phosphate trihydrate as phosphate source has the advantage that it acidifies the medium and therefore obviates the need for a separate acid to adjust the medium to a pH value of about 2.

In a preferred embodiment, glucose is used as the carbon source. The glucose is converted to β-1,3-scleroglucan, biomass, $CO_2$ and oxalic acid, which is the only detectable by-product.

To this basic medium are preferably added citric acid hydrate, preferably in an amount ranging from 0.2 to 1.5 g/l; thiamine or a mineral acid salt thereof, preferably in an amount ranging from 0.3 to 30 mg/l; and a zinc salt such as zinc sulfate, preferably in an amount ranging from 0.3 to 30 mg/l. While the yeast extract per se is a source of both thiamine and zinc, yeast extract does not provide these ingredients in sufficient amounts to provide optimum yields of the desired β-1,3-scleroglucan product.

It has been found that, by reducing the amount of oxygen used, the amounts of $CO_2$ and biomass formed are reduced, with consequent increased formation of the desired β-1,3-scleroglucan. Accordingly, it is preferred to operate the process of the present invention using a specific oxygen uptake rate (oxygen uptake rate based on the biomass) within the range of from 0.01 to 0.08 $h^{-1}$.

It is surprising that the yields of the desired β-1,3-scleroglucan product are increased when the oxygen uptake rate decreases continuously during the cultivation process, so that the oxygen supply to the cells deteriorates continuously. An explanation could be that, since the organism prefers a microaerobic environment, it surrounds itself, even "in vivo", with a mucous skin, which greatly inhibits the oxygen transfer. Consequently, its actual requirement for oxygen may be far less than the microaerobic oxygen supply in the reactor. This is consistent with the observed result that, on increasing the oxygen supply to the reactor, the oxygen serves to excessively consume the glucose by respiration, resulting in increased growth and decreased yield coefficient (g biomass per g of scleroglucan).

Preferably, a nitrogen-limited cultivation preculture (inoculum) is used. Surprisingly, it has been found that the use of a nitrogen-limited preculture, as inoculum in the cultivation, leads to an improved product-to-biomass ratio.

By limiting the amount of nitrogen source in the cultivation medium, the ratio of the desired β-1,3-scleroglucan product to biomass is significantly greater than when cultivation is conducted using a standard inoculum. It is known that a high C/N ratio has a positive effect on the product concentration during the production of microbial polysaccharides. The present observation of the favourable effect of "reverse N-limitation" (reverse since an N-limited inoculum culture, supplied to the medium, is subsequently not N-limited, since the medium thereafter contains a sufficient N-source) has not been previously reported. A possible explanation for the favourable effect of "reverse N-limitation" could be that the organism, when it is N-limited, cannot fix the cell-wall polysaccharide inside the wall, due to a deficiency of chitin, which contains nitrogen as N-acetylglucosamine units. Consequently, the cell-wall polysaccharide is released into the medium to a greater extent.

Accordingly, it is preferred to operate the process of the present invention using amounts of nitrogen source in the cultivation medium ranging from 0.2 to 0.8 g N/l.

As already indicated, oxalic acid is the only detectable by-product of the process of the present invention. The drop in pH value during the cultivation process of the invention is proportional to the amount of oxalic acid formed. The β-1,3-scleroglucan product and biomass concentrations are not influenced by the initial pH value applied in the process of the invention. This observation runs counter to previous findings in which substantially impaired product and biomass formation was reported using pH values below 3. Since this pH limitation does not apply to *Sclerotium rolfsii*, the cultivation process according to the present invention can be operated under fully non-sterile conditions at pH 2, apart from the separate sterilization of yeast extract.

Preferably, the cultivation process according to the present invention is effected with agitation, at 15 to 40° C.; the culture solution is then separated from the mass of cells; and the β-1,3-scleroglucan product so obtained is isolated in conventional manner.

The microbial production of β-1,3-scleroglucan using the Fungi imperfecti *Sclerotium rolfsii* ATCC 15205 is associated with the large increase in the viscosity of the medium in the reactor during the cultivation. In addition, the culture suspension shows pseudoplastic flow behaviour. The organism as well as the β-1,3-scleroglucan product are sensitive to shear.

As the reactor size increases, the importance of an adequate mixing of the highly-viscous medium rises. A reduced level of mixing leads to a strong decrease in the rate of growth and polysaccharide formation during the cultivation. In order to achieve adequate mixing in large reactors, it is standard practice to operate with high stirrer speeds. In the case of scleroglucan production, however, high mean shear rates and maximum stirrer speeds in the reactor degrade the polysaccharide. It has now been found that equally good mixing can be attained, in a comparable time, using very high gasification rates. In this way, the gasification mainly takes over the task of effecting axial mixing of the medium. High gasification rates also ensure a rotation of the highly-viscous reactor volume up to the end of the cultivation. Such a less severe mixing enables the production of a higher molecular product. The stirring device effects the necessary shearing off of the polysaccharide from the cell surfaces. The mean shear rates in the reactor preferably range from 18 to 25 $s^{-1}$ and the maximum stirrer speed preferably ranges from 0.7 to 1.0 m/s. Moreover, the high proportion of gas in the liquid leads to a lowering of the density of the total system and thus to a reduction of the viscosity.

The following Examples further illustrate the present invention.

EXAMPLE 1

A cultivation is conducted using the plant pathogenic, filamentary-growing fungus *Sclerotium rolfsii* ATCC 15205, obtained from the ATCC, Rockville, Md. U.S.A.

The following standard culture medium is made up:

| | |
|---|---|
| glucose monohydrate | 38.5 g/l |
| $NaNO_3$ | 3.0 g/l |
| $KH_2PO_4$ | 1.3 g/l |
| citric acid monohydrate | 0.7 g/l |
| KCl | 0.5 g/l |
| $MgSO_4$ heptahydrate | 0.5 g/l |
| $FeSO_4$ heptahydrate | 0.05 g/l |
| thiamine hydrochloride | 3.3 mg/l |
| $ZnSO_4$ heptahydrate | 3.3 mg/l |
| yeast extract | 1.0 g/l |
| Initial pH | 2.0. |

The pH adjustment of the medium is effected with 85% phosphoric acid before autoclaving the standard medium. The nutrient media are sterilized for 20 minutes at 121° C. and 1 bar excess pressure. The thiamine and $ZnSO_4$ solutions are added to the culture in sterile-filtered form. Moreover, 1 g/l of an antifoam is added to the reactor cultivation.

For the first preculture, 100 mls of the above standard culture medium are placed in a 500 ml Erlenmeyer flask fitted with baffle plates and sterilized. The first preculture is then inoculated with a piece of mycelium from one of the agar slant cultures and incubated aerobically for a week in the dark at 27° C. and at 100 rpm on a shaking machine in an incubation room at 40% relative humidity.

For the second preculture, 500 mls of the above standard culture medium are placed in a 2000 ml Erlenmeyer flask fitted with baffle plates and sterilized. The sterilized medium is then inoculated with 5% (w/v) of the first preculture. Since *Sclerotium rolfsii* forms large pellets under the low-shear conditions in the shaking flask, it is necessary to first homogenize (20,000 rpm, 30 s) the first preculture under sterile conditions. The second preculture is then incubated for 3–4 days under identical conditions described for the first preculture.

A cultivation is conducted at a stirrer speed of 200 rpm and a gasification rate of 0.067 v/vm in a reactor fitted with 4 INTERMIG stirrers and having the following dimensions:

| | |
|---|---|
| total volume | 1500 l |
| working volume | 1000 l |
| internal diameter | 860 mm |
| total height | 2760 mm |
| filled height | 1800 mm |
| stirrer diameter | 580 mm |
| height of stirrer blade | 125 mm |
| flow breaker breadth | 70 mm |
| wall spacing of flow breaker | 17 mm |
| ratio of filled height to internal diameter | 2.1 |
| ratio of stirrer diameter to internal diameter | 0.68. |

The maximum stirrer speed is 2.0 m/s and the mean shear rate is 50.0 s$^{-1}$. A total productivity of 2.9 g/l d is attained for a process period of 77 h, with a product end concentration of 9.2 g/l. The apparent viscosity (measured at 0.3 g/l polysaccharide and γ=0.3 s$^{-1}$) is 29 mPa s and the molecular weight of the polysaccharide is 3.0×10$^6$ /g/mol.

The molecular characterization of the β-1,3-scleroglucan product is conducted by light scattering techniques using five different polymer concentrations in 0.01N aqueous sodium hydroxide as solvent. Stock solutions are produced by dissolving appropriate amounts of the freeze-dried, powdered β-1,3-scleroglucan sample and the respective stock solutions are stirred for 1–2 days at 25° C. The static and dynamic light scattering data are then determined. From these data, is derived the ratio ($R_g/R_h$) of the radius of gyration ($R_g$) to the hydrodynamic radius ($R_h$). This ratio ($R_g/R_h$) serves as an indicator of the shape of the test sample. After a storage time of 11 days, the ratio ($R_g/R_h$) obtained is 0.87, which is closer to the value for a sphere (0.76) than for a rod (>2), and the second osmotic virial coeffecient ($A_2$), which describes the concentration dependence of the scattering intensity, is 4×1×10$^{-4}$ cm$^3$ molg$^{-2}$.

Viscosity measurements are carried out at 25° C. on various diluted samples of the stock solution using aqueous sodium hydroxide or dimethylsulfoxide as solvent. The instrument used for conducting the viscosity measurements is the Ubbelohde-Capillary I (capillary constant K=0.009693), with the application of the Hagenbach correction.

Rheological measurements are conducted on the β-1,3-scleroglucan sample with a Bohlin CS-50 rheometer at 25° C. The cylinder system CS-25 is used as the measuring system. Readings are taken at four polymer concentrations (0.5%, 1%, 1.5% and 2%). The solvent used is water to which is added 2-phenoxyethanol, as stabilizer. All solutions are stored for at least 2 weeks before they are analyzed. The solutions are then concentrated by distilling off the water using a "Rotavap" at 60° C.

After a storage time of 17 days, the Staudinger Index η/100 cm$^3$/g for a 0.01 N NaOH solution of the β-1,3-scleroglucan from is 3.64 and the Staudinger Index η/100 cm$^3$/g for a dimethylsulfoxide solution of the β-1,3-scleroglucan is 5.51.

These results confirm that the β-1,3-scleroglucan has a three-dimensional crosslinked triple helix structure.

EXAMPLE 2

Using the procedure described in Example 1, a cultivation is conducted at a stirrer speed of 100 rpm and a gasification rate of 1.0 v/vm in the same reactor used in Example 1. The maximum stirrer speed is 1.0 m/s and the mean shear rate is 25.0 s$^{-1}$. A total productivity of 3.1 g/l d is attained for a process period of 98 h, with a product end concentration of 12.6 g/l. The apparent viscosity (measured at 0.3 g/l polysaccharide and γ=0.3 s$^{-1}$) is 37 mPa s and the molecular weight of the polysaccharide is 4.1×10$^6$ g/mol.

Using the conditions described in Example 1, rheological measurements are conducted on the β-1,3-scleroglucan sample from Example 2 with a Bohlin CS-50 rheometer at 25° C. The cylinder system CS-25 is used as the measuring system. Readings are taken at four polymer concentrations (0.5%, 1% and 1.5%). The solvent used is water to which is added 2-phenoxyethanol, as stabilizer. All solutions are stored for at least 2 weeks before they are analyzed. The solutions are then concentrated by distilling off the water using a "Rotavap" at 60° C. Rotation measurements are conducted at shear rates of 20/s or 100/s. The results are set out in the following Table.

TABLE 1

| Concn. of test compound | Viscosity η mPas | |
|---|---|---|
| weight % | shear rate 20 [1/s] | shear rate 100 [1/s] |
| 0.5 | 231.6 | 57.16 |
| 1.0 | 573.5 | 138.2 |
| 1.5 | 1226.0 | 291.5 |

The results demonstrate pseudoplastic flow behaviour of the test compound by decreased shear viscosity at higher shear rates. To attain a good storage stability for an end product, e.g. a cosmetic formulation, the good thickening property of the new β-1,3-scleroglucans of the present invention can be utilised. In this respect, the rheological behavior of the new β-1,3-scleroglucans at low shear rates is relevant. High storage stability is also achieved by a viscosity development for which high values are obtained at low shear rates. In the case of a cosmetic paste which needs to be rubbed on the skin, shear rates of up to 1000/s occur. In order to obtain maximal uniformity of distribution of the paste on the skin, the viscosity of the paste must be low at such higher shear rates. The results in the Table demonstrate clearly that the new β-1,3-scleroglucans of the present invention satisfy these demands.

EXAMPLE 3

A massage cream is formulated from the following ingredients:

2% bees wax
45% liquid paraffin
3% cetyl alcohol
2.5% pectin (mol. weight 100,000)
46.5% deionised water
0.2% methylparaben
0.5% β-1,3-scleroglucan from Example 1 and
0.3% perfume each by weight, based on the total weight of the cream.

A first solution is prepared by homogeneously dissolving the pectin, methylparaben and glucan in the deionised water at 80° C. A second solution is produced by melting the bees wax, liquid paraffin and cetyl alcohol by heating the mixture to 80° C. While the first solution is stirred in a homomixer, the second solution is added to it and dispersed in it. The resulting emulsion is allowed to cool and, on reaching 70° C., the perfume is added. Stirring is stopped once the temperature falls to 30° C. The oil-in-water form massage cream so obtained has good texture and gloss and is stable at 2–60° C. over 6 months.

EXAMPLE 4

An aqueous ophthalmological preparation is formulated from the following ingredients:

1 mg β-1,3-scleroglucan from Example 1
1 mg Sodium Diclofenac
50 mg Solution aid (Cremophor EL)
6 mg Ophthalmological buffer (Trometamol)
19 mg Boric acid
0.04 mg Ophthalmological preservative (Thiomersal)
Water for injection purposes to 1.00 ml.

EXAMPLE 5

An aqueous lotion for the treatment of skin roughness is formulated from an aqueous emulsion containing 10% by weight of glyceryl stearate and either 0.05% or 0.50% by weight of the β-1,3-scleroglucan from Example 1.

The determination of skin roughness is conducted according to German standard DIN 4768ff. The roughness of the skin is determined by taking silicone-based skin impressions and then measuring the surface profile of the impressions, using computer-aided profilometry. The skin roughness is calculated from the multiple measuring points (100 points per square millimeter). The number of volunteers used is 10. The determination of skin roughness is conducted both prior to application of the test lotion and 8 hours after application of the test lotion. The skin of the forearm is used as the skin test area. For the purpose of comparison, a control experiment is conducted using a placebo.

The results obtained show a reduction of skin roughness (relative to untreated skin) of 32% for the lotion containing 0.05% by weight of the β-1,3-scleroglucan from Example 1 and 35% for the lotion containing 0.50% by weight of the β-1,3-scleroglucan from Example 1. The control experiment showed a reduction of skin roughness (relative to untreated skin) of only 22%.

EXAMPLE 6

The skin moisturising activity of the β-1,3-scleroglucan from Example 1 (0.1% or 0.5%) dissolved in water is investigated under defined climatic conditions (22° C. and 60% relative humidity). The test solutions are applied to the forearm. Skin moisture ratings are determined prior to application of the test solution, 1 hour after application and 8 hours after application. The determinations are conducted using a Corneometer (model CM820-Courage & Khazuka, Germany). The percentage increase of skin moisture in the treated skin area relative to untreated skin is calculated. The number of volunteers used is 10.

The increase in skin moisture, 1 hour after application, for the 0.1% aqueous solution of the β-1,3-scleroglucan from Example 1 is 27%, and for the 0.5% aqueous solution of the β-1,3-scleroglucan from Example 1 is 29%. The increase in skin moisture, 8 hours after application, for the 0.1% aqueous solution of the β-1,3-scleroglucan from Example 1 is 17% and for the 0.5% aqueous solution of the β-1,3-scleroglucan from Example 1 is 22%.

These results demonstrate that the β-1,3-scleroglucan from Example 1 shows a strong immediate increase in skin moisture. 8 hours after the application of the test product, the 0.5% solution shows excellent long-lasting water retention on the skin. This long-lasting performance is superior to comparative results obtained using, as active ingredient, either 0.1% hyaluronic acid or 0.25% collagen.

EXAMPLE 7

The anti-inflammatory activity of the β-1,3-scleroglucan from Example 1 (0.1%) dissolved in water is investigated.

The five volunteers refrained from application of cosmetic products on to the test skin area for three days prior to the start of the study. Several UV-erythema are induced on the backs of the volunteers by exposure to a UV-lamp (Ultra-Vitalux lamp; Osram). The energy applied corresponds to the 1.5-fold minimum erythema dose (MED) which is determined for each volunteer prior to the induction of the erythema. The test compound is applied immediately and 6 hours after radiation exposure. During the following 5 days, the erythema is treated twice per day with the test product. The degree of redness of the erythema is determined, using a chromameter (Minolta), 24 hours, 72 hours and 120 hours after the first application of the test product.

After 24 hours, the reduction of redness, in comparison to an untreated control erythema, is 17%; after 72 hours 23%; and after 120 hours 31%. These results are similar to, and indeed after 120 hours are superior to those obtained in comparative trials using the known anti-inflammatory agents D-panthenol (used as a 2.0% lotion) or Aloe vera (10% of a 1:1 gel). When using a lotion made from 0.5% of the β-1,3-scleroglucan from Example 1 dissolved in water, the reduction of redness, in comparison to an untreated control erythema, is 40% after 120 hours, which is far superior to the values observed using D-panthenol (used as a 2.0% lotion) or Aloe vera (10% lotion of a 1:1 gel).

EXAMPLE 8

Mouthwash Formulation

| Ingredients: | |
| --- | --- |
| 0.03-0.1% b.w. | Triclosan |
| 10–20% b.w. | alcohol (ethyl alcohol food grade) |
| 5–10% b.w. | glycerin |
| 1–2% b.w. | surfactant, e.g. Polysorbate 20/Poloxymer |

-continued

| Ingredients: | |
|---|---|
| | 407/Sodium lauryl sulfate |
| 0.02–0.05% b.w. | sodium saccharin |
| 0–0.05% b.w. | sodium fluoride |
| q.s. | flavor |
| q.s. | colour |
| ad 100% | deionized water |
| adjusted to pH 5–7 | |
| 1–5% b.w. | β-1,3-scleroglucan from Example 1. |

Preparation method: Triclosan is dissolved in alcohol, then the surfactant is added as solution. Glycerin and about 20% of the water are added to this solution. All other ingredients are then added and stirred until homogenization. Water is then added to 100%. PH-value is then adjusted and stirred until the solution becomes clear.

If Triclosan is not dissolved completely, the content of alcohol and/or surfactant must be increased.

EXAMPLE 9

Toothpaste Formulation

| Ingredients: | |
|---|---|
| 0.1–0.3% b.w. | anti-gingivitis/anti-bacierial agent, like Triclosan, |
| 0.1–1.0% b.w. | anti-caries agents, like sodium fluoride, sodium monofluorophosphate |
| 1.0% b.w. | gelling agents like carboxymethylcellulose, hydroxyethylcellulose or xanthan gum, |
| 10–20% b.w. | humectants, like glycerin, sorbitol 70% or propylene glycol, |
| 15–20% b.w. | abrasives like calcium carbonate, hydrated silica, dicalcium phosphate dihydrate or alumina, |
| 0.1–0.2% b.w. | sweetener like saccharin, |
| 1.0–1.5% b.w. | flavors like spearmint, peppermint, menthol or vanillin, |
| 1.0–2.0% b.w. | surfactants like sodium lauryl sulfate, sodium lauroyl sarcosinate or sodium lauryl sulfoacetate |

-continued

| Ingredients: | |
|---|---|
| 0.1–0.5% b.w. | preservative like parabens |
| q.s. | colour |
| ad 100 % | water |
| 5–10% b.w. | β-1,3-scleroglucan from Example 1. |

What is claimed is:

1. A cosmetic composition comprising:
   A) a cosmetically acceptable carrier; and
   B) 0.05 to 3.0% by weight, based on the weight of the total composition of a β-1,3-scleroglucan having a three-dimensional crosslinked triple helix structure and having a mean molecular weight of $1 \times 10^6$ to $12 \times 10^6$ obtained from cultivating the plant-pathogenic fungi imperfecti *Sclerotium rolfsii* ATCC 15205 in a culture medium under microaerobic conditions.

2. A composition according to claim 1 in which the composition constitutes a shampoo and/or hair conditioner composition.

3. A composition according to claim 1 in which the composition is a skin care composition.

4. A composition according to claim 3 in which the skin care composition is formulated as an aqueous lotion, a water-in-oil or an oil-in-water emulsion, an oil or oil-alcohol lotion, a vesicular dispersion of an anionic or nonionic amphiphilic lipid, an aqueous, aqueous-alcohol, alcohol or oil-alcohol gel, a solid stick or an aerosol.

5. A composition according to claim 4 in which, in a water-in-oil or an oil-in-water emulsion, the cosmetically acceptable carrier A) comprises 5 to 50% of an oil phase and 47 to 94.95% of water, each based on the total weight of the composition.

6. A composition according to claim 1 in which the composition constitutes an anti-inflammatory skin care preparation.

7. A composition according to claim 6 in which the anti-inflammatory skin care preparation is an after-sun skin care preparation.

8. A composition according to claim 1 in which the composition constitutes an oral care preparation; a mucosal lubricant formulation; or an ophthalmological preparation comprising a carrier.

\* \* \* \* \*